US009282939B2

(12) United States Patent
Tajima et al.

(10) Patent No.: US 9,282,939 B2
(45) Date of Patent: Mar. 15, 2016

(54) RADIATION IMAGING APPARATUS

(71) Applicant: FUJIFILM Corporation, Tokyo (JP)

(72) Inventors: Takashi Tajima, Kanagawa (JP); Yusuke Kitagawa, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 14/728,300

(22) Filed: Jun. 2, 2015

(65) Prior Publication Data

US 2015/0257723 A1 Sep. 17, 2015

Related U.S. Application Data

(62) Division of application No. 14/582,931, filed on Dec. 24, 2014, now Pat. No. 9,072,485, which is a division of application No. 13/599,260, filed on Aug. 30, 2012, now Pat. No. 8,956,045.

(30) Foreign Application Priority Data

Sep. 30, 2011 (JP) ................................ 2011-216602

(51) Int. Cl.
| | | |
|---|---|---|
| *G01D 18/00* | (2006.01) | |
| *G21K 1/00* | (2006.01) | |
| *A61B 6/00* | (2006.01) | |

(52) U.S. Cl.
CPC ............... *A61B 6/4283* (2013.01); *A61B 6/542* (2013.01); *A61B 6/56* (2013.01); *G01D 18/00* (2013.01)

(58) Field of Classification Search
CPC ...... A61B 6/4283; A61B 6/56; A61B 6/4291; A61B 6/547
USPC .............. 378/41, 42, 51, 62, 91, 95, 98, 98.8, 378/145, 162, 165, 166, 189, 190, 193, 197, 378/210
See application file for complete search history.

(56) References Cited

U.S. PATENT DOCUMENTS

| | | | | | |
|---|---|---|---|---|---|
| 5,666,395 | A | * | 9/1997 | Tsukamoto | A61N 5/103 250/370.09 |
| 5,844,961 | A | * | 12/1998 | McEvoy | A61B 6/4494 348/E5.086 |
| 6,196,715 | B1 | * | 3/2001 | Nambu | A61B 6/00 378/11 |
| 6,282,264 | B1 | * | 8/2001 | Smith | A61B 6/0457 378/167 |
| 6,851,851 | B2 | * | 2/2005 | Smith | A61B 6/0457 378/167 |
| 7,857,511 | B2 | * | 12/2010 | Hesl | A61B 6/4233 378/189 |
| 7,989,773 | B2 | * | 8/2011 | Jadrich | G01T 1/20 250/370.09 |
| 8,447,011 | B2 | * | 5/2013 | Ohta | A61B 6/00 378/62 |
| 8,550,709 | B2 | * | 10/2013 | Nishino | A61B 6/04 378/145 |

(Continued)

FOREIGN PATENT DOCUMENTS

JP 2007-007251 1/2007

*Primary Examiner* — David A Vanore
(74) *Attorney, Agent, or Firm* — Young & Thompson

(57) ABSTRACT

A cassette holder of an imaging stand is provided with first and second catch members for catching and holding an electronic cassette from above and below. The first catch member has a multi connector connected to a multi terminal of the electronic cassette. The multi connector is offset with respect to a center line of an imaging surface of the cassette holder. The multi terminal is offset with respect to a center line of an irradiation surface of the electronic cassette in the same direction by the same amount as those of the multi connector. In a state where said electronic cassette mounted on a tray is loaded into the cassette holder, the center line of the irradiation surface coincides with the center line of the imaging surface.

11 Claims, 13 Drawing Sheets

(56) References Cited

U.S. PATENT DOCUMENTS

| | | | | |
|---|---|---|---|---|
| 8,704,188 B2* | 4/2014 | Kitano | A61B 6/548 | 250/370.09 |
| 8,714,817 B2* | 5/2014 | Oyaizu | G03B 42/04 | 378/189 |
| 2009/0122959 A1* | 5/2009 | Jadrich | G01T 1/20 | 378/91 |
| 2011/0110497 A1 | 5/2011 | Nishino et al. | | |
| 2012/0314838 A1* | 12/2012 | Oyaizu | G03B 42/047 | 378/62 |
| 2013/0077744 A1* | 3/2013 | Kamiya | A61B 6/5241 | 378/62 |
| 2013/0083898 A1* | 4/2013 | Tajima | A61B 6/4283 | 378/97 |
| 2013/0114790 A1* | 5/2013 | Fabrizio | A61B 6/02 | 378/62 |
| 2013/0136235 A1* | 5/2013 | Liu | A61B 6/4233 | 378/98 |
| 2013/0182823 A1* | 7/2013 | Kuwabara | A61B 6/542 | 378/62 |
| 2013/0202086 A1* | 8/2013 | Tsuji | G01T 1/026 | 378/62 |
| 2013/0251110 A1* | 9/2013 | Kim | G03B 42/04 | 378/189 |
| 2014/0072103 A1* | 3/2014 | Kitano | A61B 6/4233 | 378/62 |
| 2014/0086391 A1* | 3/2014 | Ohta | A61B 6/4233 | 378/91 |

* cited by examiner

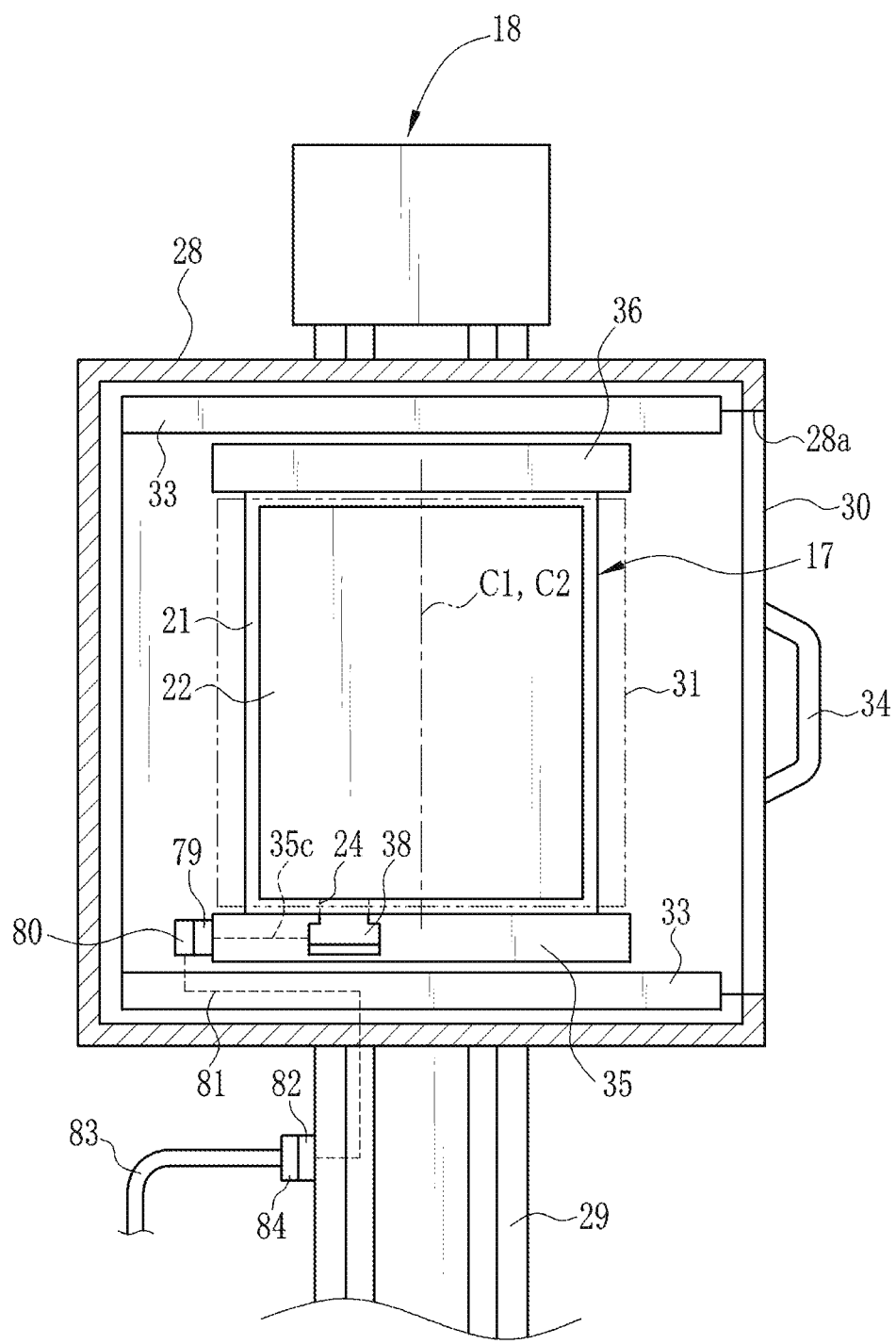

RADIATION IMAGING APPARATUS

BACKGROUND OF THE INVENTION

1. Field of the Invention

The present invention relates to a radiation imaging apparatus having an electronic cassette and an imaging stand that holds the electronic cassette.

2. Description Related to the Prior Art

In a medical field, a radiation image capturing system, for example, an X-ray image capturing system is constituted of an X-ray generating apparatus for generating X-rays and an X-ray imaging apparatus for taking an X-ray image by reception of the X-rays. The X-ray generating apparatus includes an X-ray source for emitting the X-rays to a patient's body, a source controller for controlling the operation of the X-ray source, and an exposure switch for inputting an emission start command of the X-rays. The X-ray imaging apparatus has an electronic cassette, which receives the X-rays having passed through the patient's body and produces the X-ray image.

The electronic cassette is composed of a flat panel detector (FPD) and a flat rectangular housing containing the FPD. The FPD has a matrix of pixels each of which accumulates signal charge by an amount corresponding to the amount of the X-rays incident thereon. The FPD accumulates the signal charge by a pixel-by-pixel basis, and converts the accumulated signal charge into a voltage signal in its signal processing circuit. Thereby, the FPD electrically detects the X-ray image, and outputs the X-ray image as digital image data.

The electronic cassette is used in a state of being mounted on an imaging stand. Also in some cases, the electronic cassette is used in a state of being put on a bed or held by a patient himself/herself to take the X-ray image of a body part that is hard to take in a stationary state. The electronic cassette is sometimes brought out from a hospital for use in bedside radiography of a home-care patient or in an accident or natural disaster site in an emergency.

Some electronic cassettes are provided with both a wired communicator using a communication line e.g. a cable as a transmission line and a wireless communicator using an electromagnetic wave as the transmission line, in order to transmit and receive various signals including a control signal and an image data signal to and from an external device disposed outside the imaging stand. The wireless communicator is adopted when portability is required of the electronic cassette, for example, in the case of the bedside radiography. The wired communicator is adopted when communication reliability is required, e.g. in the case of using an automatic exposure control (AEC) function. In the AEC function, a dosimeter provided in the electronic cassette measures an X-ray dose passed through the patient's body. When the X-ray dose reaches a threshold value, an emission stop signal is transmitted to the X-ray source to stop X-ray emission. Since delay in transmission of the emission stop signal causes an excessive dose to the patient, the AEC function uses the wired communicator that is superior in transmission stability and transmission speed to the wireless communicator.

In wired communication, as a matter of course, the electronic cassette and the external device are connected through a communication cable, a relay cable, connection terminals, connectors, and the like to establish the wired transmission line. For example, to establish the wired communication between the electronic cassette and the external device, one end of the communication cable is connected through the connector to the connection terminal provided in a side surface of the housing of the electronic cassette, while the other end of the communication cable is connected to the external device. If the electronic cassette is used without being mounted on the imaging stand, all outer surfaces of the housing of the electronic cassette are exposed to the outside, so nothing hinders access to the connection terminal.

On the other hand, if the electronic cassette is used with being mounted on the imaging stand, the imaging stand covers the electronic cassette at least at a part of the side surface of the housing. Thus, when trying to connect the communication cable to the connection terminal of the electronic cassette mounted on the imaging stand, the imaging stand possibly hinders access to the connection terminal, though it depends on the position of the connection terminal, and prevents the connection of the communication cable. In such a case, the electronic cassette is firstly connected with the communication cable, and then is mounted on the imaging stand.

However, when trying to mount the electronic cassette with the communication cable on the imaging stand, the communication cable sometimes interferes with the mounting and needs routing, and brings about a troublesome task. Furthermore, since a magnet the fixed power of which is not so strong is generally used for fixing the connector of the communication cable to the connection terminal of the electronic cassette due to its ease of mating and unmating, the connector is possibly unmated from the connection terminal during the mounting or during moving the imaging stand with the electronic cassette. If radiography is performed without notice of the unmating of the connector from the connection terminal, the AEC function does not work appropriately, so the patient receives an excessive X-ray dose. On the other hand, if the connector is firmly locked in the connection terminal using claws, when the communication cable gets snagged in moving the imaging stand, the connection terminal and the connector easily break.

US Patent Application Publication No. 2011/0110497 discloses a rack and a bed that hold an electronic cassette at their holders. The holder is provided with a connection terminal for connecting the electronic cassette to an external device through a communication cable. When the electronic cassette is held by the rack or the bed, a connection terminal of the electronic cassette is connected to the connection terminal of the holder.

The electronic cassette comes in sizes of 17 inches by 14 inches, 17 inches by 17 inches, and the like, but it is expected to have greater variation in size. Therefore, it is desired that the imaging stand is ready for the electronic cassettes of various sizes. However, the holder of the US Patent Application Publication No. 2011/0110497 is compliant with only a single size of electronic cassette, so another size of electronic cassette cannot be mounted thereon. Even if an incompliant size of electronic cassette is mounted on the holder of the US Patent Application Publication No. 2011/0110497, the center of an irradiation surface of the electronic cassette deviates from the center of an imaging surface of the rack, because the connection terminal is provided in the side surface of the holder.

Japanese Patent Laid-Open Publication No. 2007-007251 discloses an imaging table in which a pair of arms catches opposed side surfaces of a cassette to place the cassette in proper position. Various sizes of cassettes can be mounted on this imaging table. However, this imaging table is designed for a conventional film cassette and IP cassette, and hence is not intended to have a connector for connection to the electronic cassette.

SUMMARY OF THE INVENTION

An object of the present invention is to provide a radiation imaging apparatus in which even if any size of electronic cassette is mounted on an imaging stand, the electronic cassette is properly positioned in the imaging stand with ease, and is easily connected through a cable to an external device provided outside the imaging stand.

To achieve the above and other objects of the present invention, a radiation imaging apparatus according to the present invention includes an irradiation surface, a connection terminal, an imaging surface, first and second catch members, and a connector. The irradiation surface is formed in a surface of a housing of an electronic cassette to receive irradiation with radiation. The connection terminal is provided in a first side surface of the housing. The first side surface is orthogonal to the irradiation surface. The imaging surface is provided in an imaging stand. The imaging surface faces the irradiation surface in a state where the electronic cassette is mounted on the imaging stand. The first and second catch members are provided in the imaging stand. The first and second catch members catch the electronic cassette with contacting the first catch member to the first side surface of the housing and contacting the second catch member to a second side surface opposed to the first side surface, to hold the electronic cassette in a state of facing the irradiation surface to the imaging surface. The connector is provided in the first catch member. The connector is connected to the connection terminal, when the electronic cassette is mounted on the imaging stand. The positional relation including a distance and a direction of the connector with respect to a center line of the imaging surface is the same as that of the connection terminal with respect to a center line of the irradiation surface of the electronic cassette. The center line of the irradiation surface and the center line of the imaging surface extend in the same direction, when the electronic cassette is mounted on the imaging stand.

The first and second catch members preferably extend in a direction orthogonal to the center line of the imaging surface.

The connection terminal is preferably offset with respect to the center line of the irradiation surface. The connector is preferably offset with respect to the center line of the imaging surface by the same amount in the same direction as those of the connection terminal.

The connection terminal may be disposed above the center line of the irradiation surface, and the connector may be disposed above the center line of the imaging surface.

The imaging stand preferably includes a cassette holder having the imaging surface and a tray having the first and second catch members. The tray may be insertable into and pullable out of the cassette holder. A catch of the electronic cassette with the first and second catch members may allow connection between the connection terminal and the connector and mounting of the electronic cassette on the tray. The center line of the irradiation surface coincides with the centerline of the imaging surface, when the tray is loaded into the cassette holder in a state of connecting the connection terminal and the connector.

The connection terminal may be a female terminal, and the connector may be a male connector. The connector may be movable between a retracted position and a projected position. In the retracted position, the connector is not projected from a catch surface of the first catch member. In the projected position, the connector is projected from the catch surface, and the catch surface of the first catch member contacts the first side surface of the electronic cassette. The connector may be moved to the projected position when being connected to the connection terminal.

In another case, the connection terminal may have a flat contact surface coplanar to the first side surface, and the connector may have a flat contact surface coplanar to the catch surface of the first catch member. When the first and second catch members catch the electronic cassette with contacting the catch surface of the first catch member to the first side surface, the connection terminal and the connector are connected by contact between the flat contact surfaces.

The imaging stand preferably has an external connection terminal extending from an external device disposed outside the imaging stand to electrically connect the electronic cassette to the external device through the connection terminal and the connector. The external connection terminal may be provided in the first catch member. The imaging stand may have at least one relay terminal for relaying between the external connection terminal and the connector. The relay terminal may include a first relay terminal provided in the first catch member and a second relay terminal provided in the cassette holder. The first and second relay terminals may be connected by loading the tray into the cassette holder. The first and second relay terminals may be disconnected by unloading the tray from the cassette holder.

The electronic cassette may include an automatic exposure controller. The automatic exposure controller may include a dosimeter, a controller, and a communicator. The dosimeter measures a dose of the radiation emitted from a radiation source and passed through a human body. The controller compares a measurement result of the dosimeter with a threshold value. The communicator is established by connection between the connection terminal and the connector. If the measurement result reaches the threshold value, the controller sends an emission stop signal through the communicator to the radiation source to stop emission of the radiation.

The connection terminal and the connector may connect the electronic cassette to the external device that controls the electronic cassette in order to establish communication between the electronic cassette and the external device. In another case, the connection terminal and the connector may connect the electronic cassette to the external device in order to supply electric power from the external device to the electronic cassette.

The connection terminal may be a multi terminal that is integrally formed with a communication terminal for communicating with the external device and a power terminal for supplying electric power to the electronic cassette. The connector may be a multi connector that is integrally formed with a communication connector for communicating with the external device and a power connector for supplying the electric power to the electronic cassette.

The first and second catch members preferably catch the electronic cassette from above and below.

According to the present invention, the positional relation including the distance and the direction of the connection terminal with respect to the center line of the electronic cassette is the same as that of the connector with respect to the center line of the imaging stand. Therefore, even if the electronic cassette of any size is mounted on the imaging stand, the electronic cassette is properly positioned in the imaging stand with ease. Moreover, the electronic cassette is easily connected through a cable to the external device disposed outside the imaging stand.

BRIEF DESCRIPTION OF THE DRAWINGS

For more complete understanding of the present invention, and the advantage thereof, reference is now made to the subsequent descriptions taken in conjunction with the accompanying drawings, in which:

FIG. 10 is a sectional view of an essential portion of a cassette holder according to the second embodiment;

DESCRIPTION OF THE PREFERRED EMBODIMENTS

Figure 1:
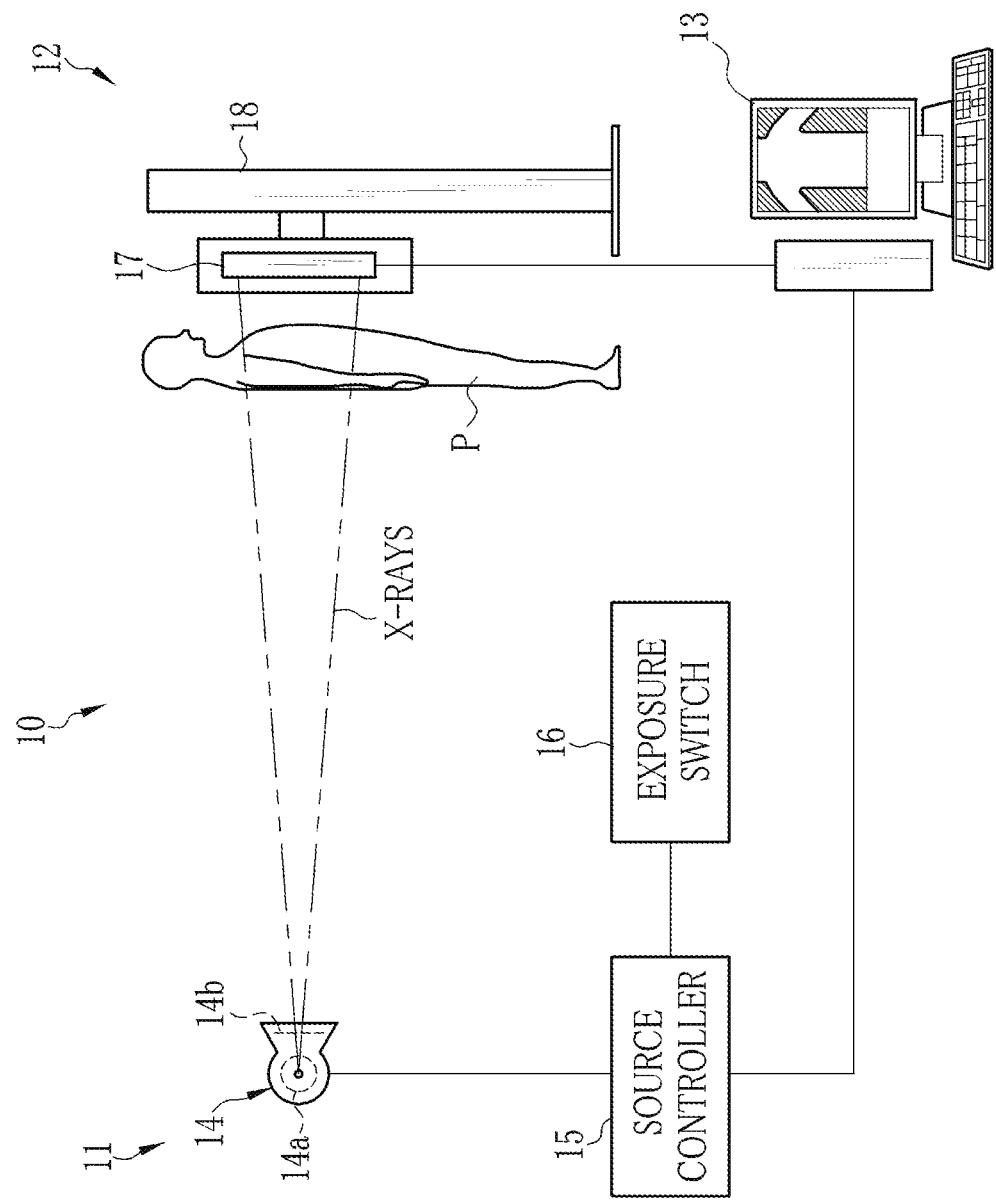
FIG. 1 is an explanatory view showing schematic structure of an X-ray image capturing system.

As shown in FIG. 1, an X-ray image capturing system 10 is constituted of an X-ray generating apparatus 11, an X-ray imaging apparatus 12, and a console 13. The X-ray generating apparatus 11 is provided with an X-ray source 14 for applying X-rays to a patient P, a source controller 15 for controlling the X-ray source 14, and an exposure switch 16 for issuing an X-ray emission command to the source controller 15. The X-ray imaging apparatus 12 is provided with an electronic cassette 17 and an imaging stand 18. The electronic cassette 17 receives the X-rays having passed through the patient P and produces an X-ray image. The imaging stand 18 holds the electronic cassette 17 in such a position as to be opposed to the patient's body portion to be examined.

The X-ray source 14 has an X-ray tube 14a for emitting the X-rays and a collimator 14b for limiting an X-ray irradiation field of the X-ray tube 14a. The X-ray tube 14a has a cathode being a filament for emitting thermoelectrons, and an anode (target) for radiating the X-rays by collision of the thermoelectrons emitted from the cathode. The target is a disk-shaped rotating anode in which rotation moves focus of the collision with the thermoelectrons in circumferential orbit to disperse heat production from the focus. The collimator 14b is composed of four X-ray shielding lead plates disposed on each side of a rectangle so as to form an irradiation opening in its middle through which the X-rays propagate. Changing the positions of the lead plates can vary the size of the irradiation opening to limit the X-ray irradiation field.

Figure 2:
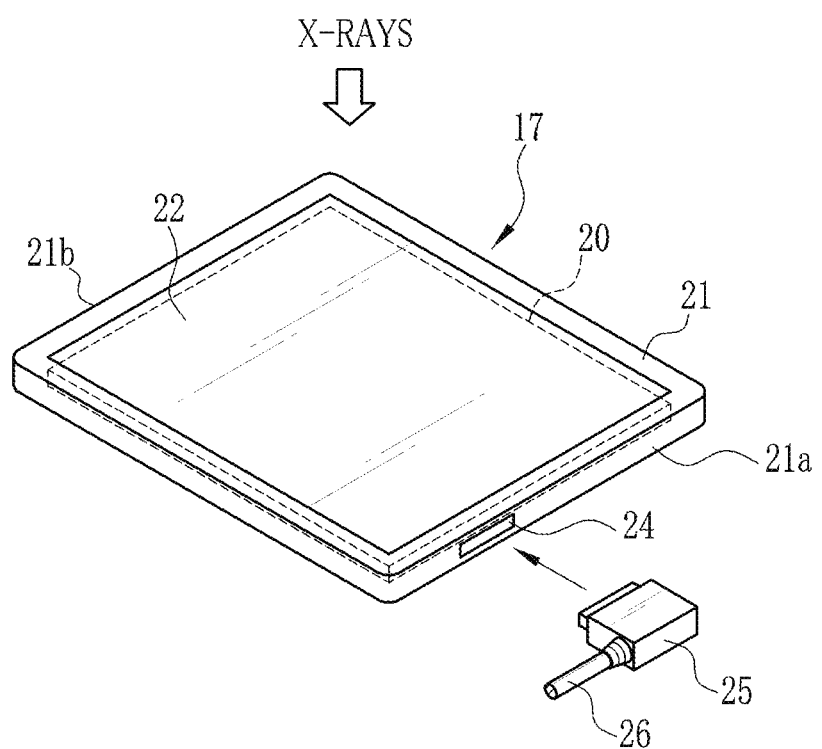
FIG. 2 is a perspective view of an electronic cassette and a multi connector.

As shown in FIG. 2, the electronic cassette 17 is composed of an FPD 20 and a flat rectangular housing 21 containing the FPD 20. The housing 21 is approximately the same size as a film cassette and an IP cassette, and, for example, is 17 inches by 14 inches identical in size to the IP cassette of a half size. The housing 21 is provided at its top surface with an irradiation surface 22 to which the X-rays are applied. The irradiation surface 22 is made of an X-ray transparent material such as carbon to prevent attenuation of the X-rays to be incident on the FPD 20.

The housing 21 is provided with a rectangular multi terminal 24, which corresponds to a connection terminal, at its first side surface 21a being one of short side surfaces. The multi terminal is integrally formed with a communication terminal for establishing wired communication with an external device such as the console 13 and a power terminal for supplying electric power from the console 13 to the electronic cassette 17. The multi terminal 24 is a female terminal recessed on the side surface of the housing 21.

A male multi connector 25 is fitted into the multi terminal 24 for connection. The multi connector 25 is integrally formed with a communication connector for establishing communication between the electronic cassette 17 and the external device such as the console 13 and a power connector for supplying the electric power to the electronic cassette 17. A multi cable 26, which is integrally formed with a communication cable for establishing communication between the electronic cassette 17 and the external device and a power cable for supplying the electric power to the electronic cassette 17, is attached to the multi connector 25. The multi connector 25 is fixed to the multi terminal 24 with magnets provided at ends of the multi terminal 24 and the multi connector 25, for example, to facilitate mating and unmating. Note that, the electronic cassette 17 has a wireless communication function, in addition to a wired communication function using the multi connector 25.

Figure 3:
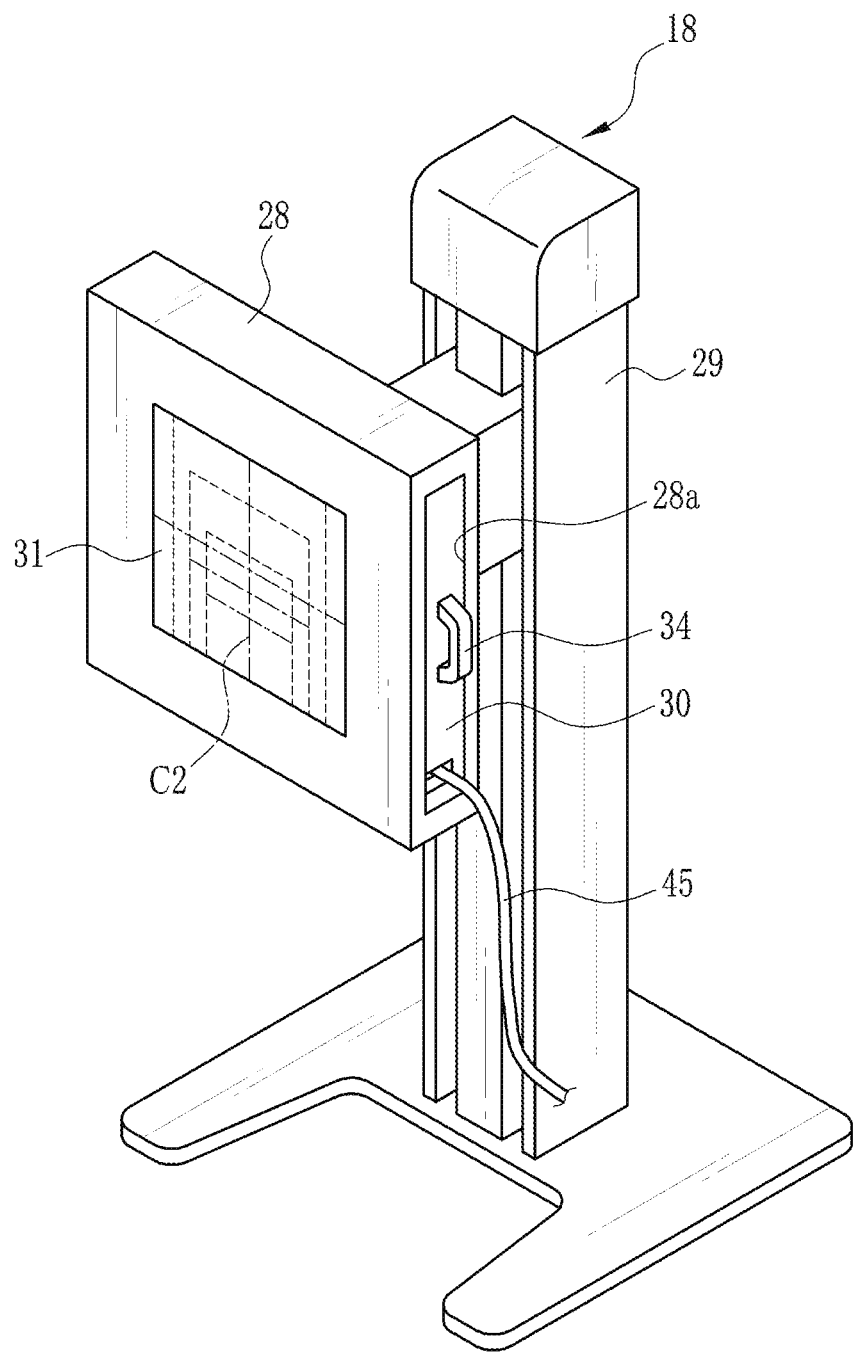
FIG. 3 is a perspective view of an imaging stand.

As shown in FIG. 3, the imaging stand 18 is provided with a cassette holder 28 for holding the electronic cassette 17 mounted on a tray 30 and a column 29 for supporting the cassette holder 28 movably upward and downward. The cassette holder 28 is provided with a tray insertion slot 28a at its side surface. The tray 30 is loaded into the cassette holder 28 through the tray insertion slot 28a. The cassette holder 28 has an imaging surface 31 at its front surface. The imaging surface 31 is opposed to the electronic cassette 17 mounted on the tray 30. In the imaging surface 31, imaging areas that vary in accordance with the size of the electronic cassette mounted on to the tray 30 and a center line C2 representing the center of each imaging area are printed. The electronic cassette 17 is aligned with the imaging stand 18 with respect to the center line C2.

Figure 4:
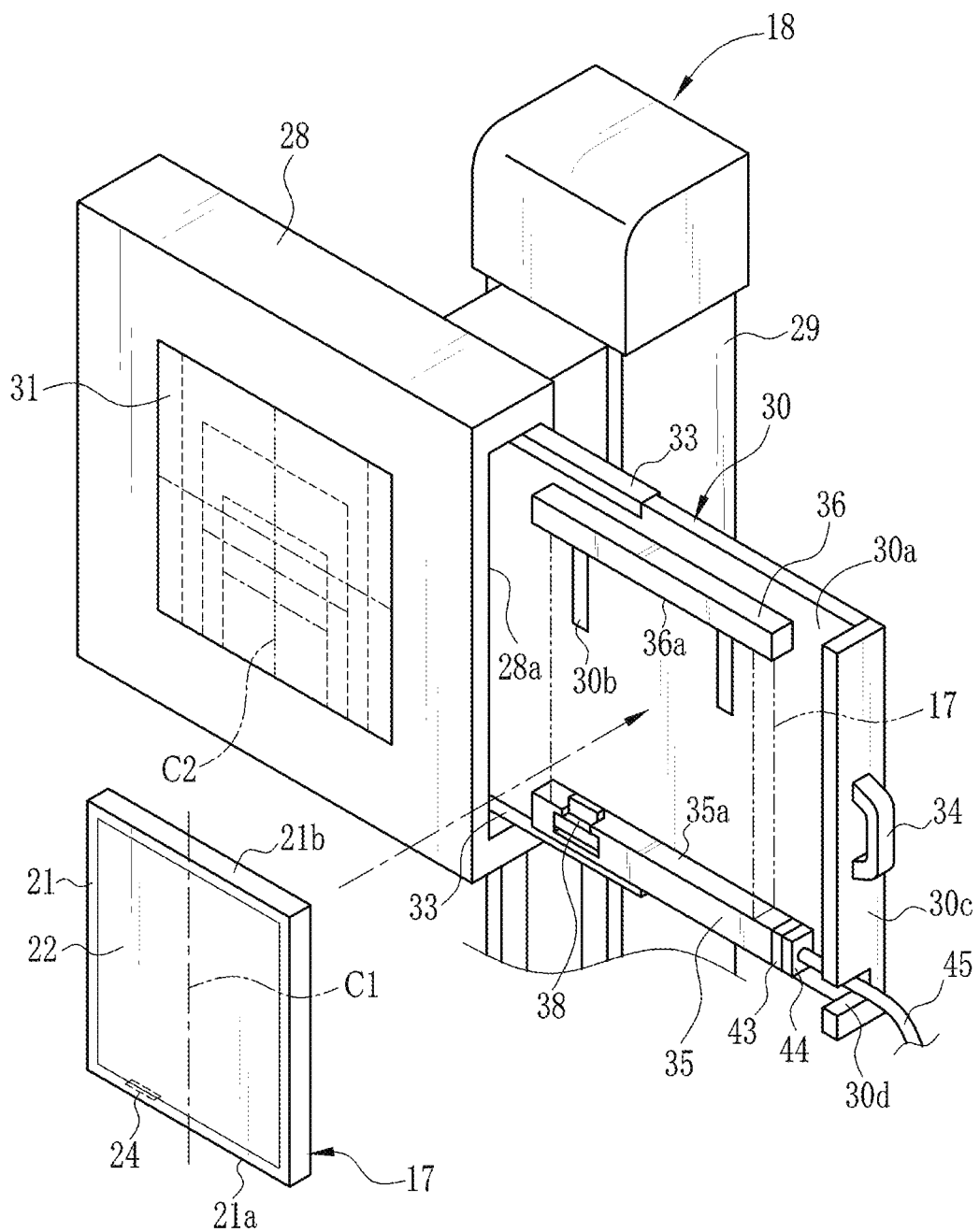
FIG. 4 is a perspective view of the imaging stand in a state of pulling out a tray.
Figure 5:
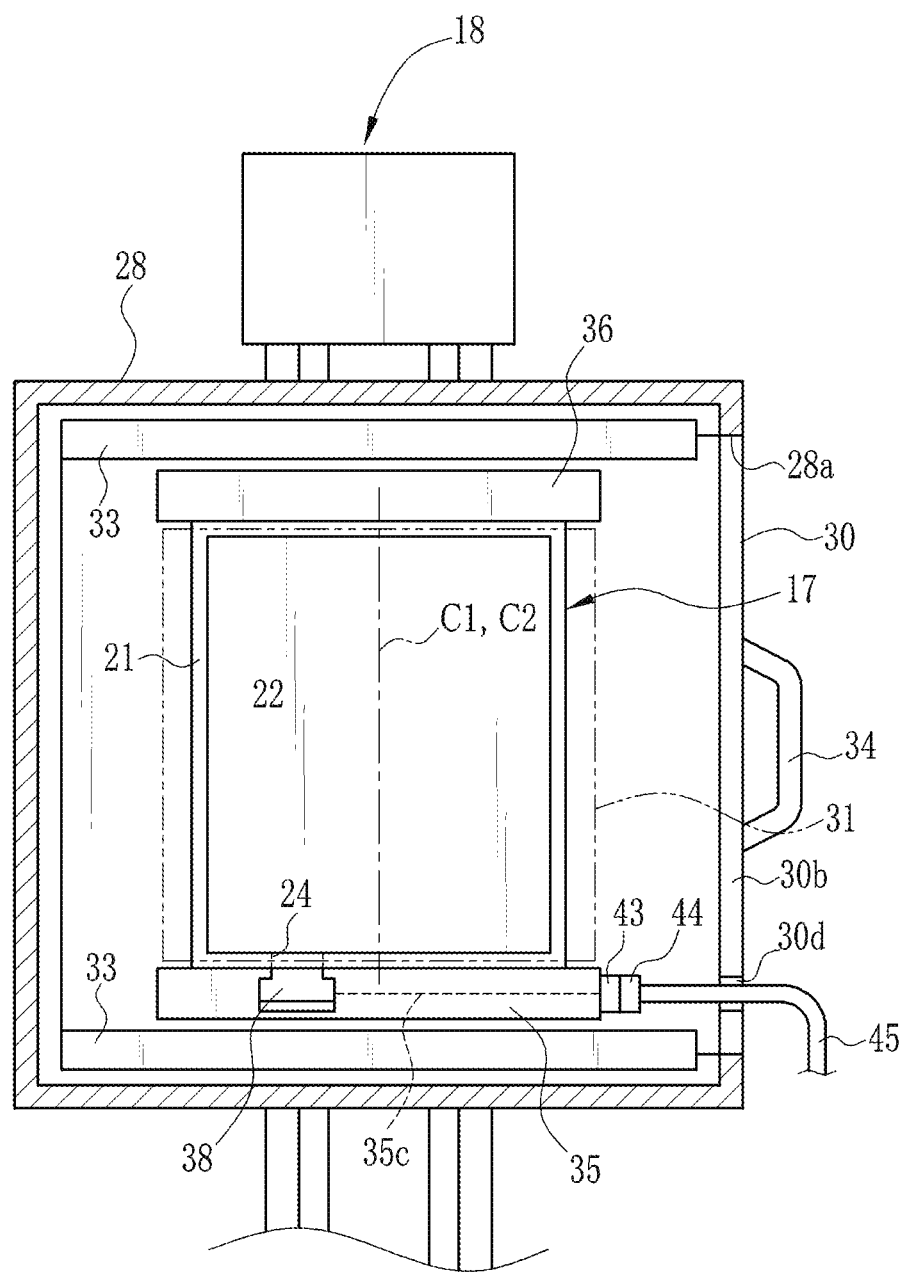
FIG. 5 is a sectional view of an essential portion of a cassette holder.

As shown in FIG. 4, upper and lower edges of the rectangular board-shaped tray 30 are guided by rails 33 provided in interior upper and lower sides of the cassette holder 28, respectively. Using a grip 34 attached to a side board 30c, the tray 30 is pulled out of the cassette holder 28 in a lateral direction. A front side of the tray 30 is formed with a mount board 30a on which the electronic cassette 17 is detachably mounted. As shown in FIG. 5, in a state where the tray 30 is loaded into the cassette holder 28, the electronic cassette 17 mounted on the tray 30 is opposed to the imaging surface 31.

The mount board 30a is provided with a first catch member 35 fixed in a lower portion of the mount board 30a and a second catch member 36 disposed in an upper portion of the mount board 30a so as to be opposed to the first catch member

35. The first and second catch members 35 and 36 extend in a direction orthogonal to the center line C2. The second catch member 36 is movable upward and downward along guide grooves 30b so as to move forward to and backward from the first catch member 35. The second catch member 36 is biased to a direction approaching the first catch member 35 by a spring provided on a rear surface of the tray 30, for example.

The electronic cassette 17 is disposed and mounted on the mount board 30a of the tray 30 in such a position that the irradiation surface 22 faces the imaging surface 31. The first and second catch members 35 and 36 catch the electronic cassette 17 from above and below in such a manner that catch surfaces 35a and 36a of the first and second catch members 35 and 36 come into contact with first and second side surfaces 21a and 21b of the housing 21, respectively.

Figure 6A:
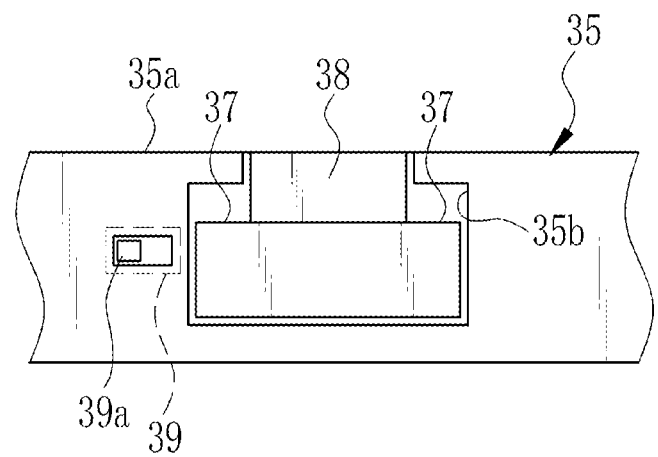
FIG. 6A is an explanatory view of a multi connector in a retracted position.

The first catch member 35 has a multi connector 38 that is connected to the multi terminal 24 of the electronic cassette 17 mounted on the tray 30. The multi connector 38, which corresponds to a connector, is integrally formed with a communication connector and a power connector, and has the same function as that of the multi connector 25. The multi connector 38 is movable between a retracted position (see FIG. 6A) and a projected position (see FIG. 6B). In the retracted position, the multi connector 38 fully retracts into a recess 35b provided in the first catch member 35. In the projected position, the multi connector 38 is projected from the catch surface 35a of the first catch member 35. The multi connector 38 has a regulating portion 37 that comes in contact with an inner wall surface of the recess 35b upon being moved to the projected position. The movement of the multi connector 38 in the direction from the retracted position to the projected position is regulated by the regulating portion 37.

The multi connector 38 is moved manually, for example. The first catch member 35 is provided with a lock mechanism 39 for locking the multi connector 38 in the retracted or projected position. The lock mechanism 39 has an engaging portion in its inside. The engaging portion protrudes into the recess 35b and engages with the multi connector 38 to lock the multi connector 38. The lock mechanism 39 has a slide switch 39a that restrains and releases the lock mechanism 39.

Before mounting the electronic cassette 17 on the tray 30, the multi connector 38 is moved to the retracted position, and the lock mechanism 39 locks the multi connector 38 in the retracted position. In this state, the first and second catch members 35 and 36 catch the electronic cassette 17 so as to align the multi terminal 24 of the electronic cassette 17 with the multi connector 38.

By a bias of the spring, the second catch member 36 presses the electronic cassette 17 against the first catch member 35. Therefore, a pressing force from the first catch member 35 is applied to the first side surface 21a of the electronic cassette 17 having the multi terminal 24. Since the direction of application of the pressing force coincides with the direction of projection of the multi connector 38, the multi connector 38 is securely connected to the multi terminal 24 by the pressing force. During this connection, the lock mechanism 39 locks the multi connector 38 in the projected position, so the multi connector 38 does not fall in the retracted position. The first catch member 35 keeps applying the pressing force even after the multi connector 38 is connected to the multi terminal 24, so the connection is hard to unmate.

In the case of mounting the film cassette or the IP cassette on the tray 30, the multi connector 38 is moved to the retracted position so as not to hinder the mounting. The lock mechanism 39 locks the multi connector 38 in the retracted position as necessary.

Figure 7A:
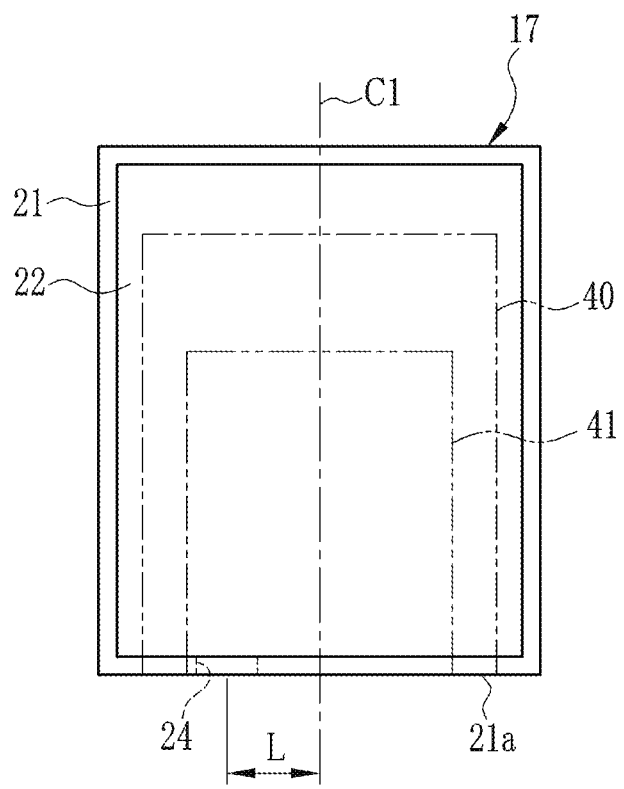
FIG. 7A is a top plan view of the electronic cassette that represents an offset position of a multi terminal with respect to a center line.

As shown in FIG. 7A, the center of the multi terminal 24 of the electronic cassette 17 in its width direction is offset by a length L to the left with respect to a center line C1 of the irradiation surface 22 orthogonal to the first side surface 21a. Thus, when the multi connector 25 of FIG. 2 is fitted into the multi terminal 24 of the electronic cassette 17, the multi connector 25 does not become an obstacle in radiography.

Figure 7B:
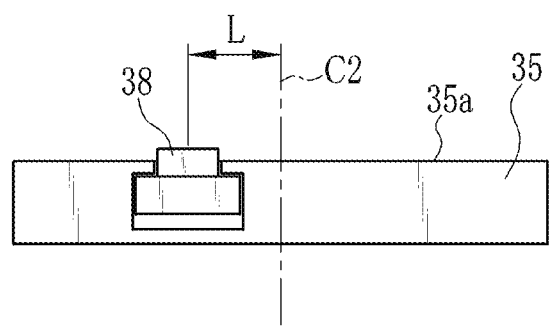
FIG. 7B is a sectional view of a first catch member and the multi connector that represents an offset position of the multi connector with respect to a center line.

As shown in FIG. 7B, when the tray 30 is loaded into the cassette holder 28, the center of the multi connector 38 of the first catch member 35 in its width direction is offset with respect to the vertical center line C2 of the imaging surface 31 by a length L to the left, that is to say, by the same amount to the same direction as those of the multi terminal 24. The center line C1 represents the center of the irradiation surface 22 in its width direction, and the center line C2 represents the center of the imaging surface 31 in its width direction. The center lines C1 and C2 extend in the same direction in a state where the electronic cassette 17 is held by the imaging stand 18. The multi connector 38 and the multi terminal 24 have the same positional relation including distance and direction with respect to the center lines C2 and C1, respectively. For this reason, in mounting the electronic cassette 17 on the tray 30, the multi terminal 24 and the multi connector 38 determine the position of the electronic cassette 17 in the width direction relative to the cassette holder 28. Therefore, it is possible to easily align the center of the irradiation surface 22 with the center of the imaging surface 31 in the width direction.

Also, as shown by a chain double-dashed line of FIG. 7A, a multi terminal of an electronic cassette 40 or 41 of size smaller than that of the electronic cassette 17 is offset by the same length L to the left with respect to the center line C1 of its irradiation surface. That is to say, even if the size of the housing and the irradiation surface is changed, the multi terminal of the electronic cassette 40 or 41 mounted on the imaging stand 18 has the same positional relation including the distance and the direction with respect to the center line C1 of the irradiation surface. Therefore, even if the electronic cassette 40 or 41 of different size is mounted on the tray 30, it is possible to easily align the center of the irradiation surface in the width direction with the center of the imaging surface 31.

As shown in FIGS. 4 and 5, an external connection terminal 43 is provided on a vertical surface of the first catch member 35 on the side of the side board 30c. To the external connection terminal 43, a multi cable 45 extending from the console 13 is connected to establish electrical connection between the console 13 being the external device disposed outside of the imaging stand 18 and the electronic cassette 17 mounted on the imaging stand 18. The external connection terminal 43 is connected to the multi connector 38 through a relay cable 35c routed through the first catch member 35. As with the multi terminal 24, the external connection terminal 43 is integrally formed with a communication terminal and a power terminal.

To the external connection terminal 43, a multi connector 44, which has the same function as that of the multi connector 25, is connected and secured by screws or the like to prevent unmating. The multi cable 45 connected to the multi connector 44 is drawn out through an opening 30d provided in the side board 30c of the tray 30 to the outside of the cassette holder 28. Another multi connector 46 (see FIG. 8) that is provided in the multi cable 45 at an end opposite to the multi connector 44 is connected to the console 13.

Figure 8:
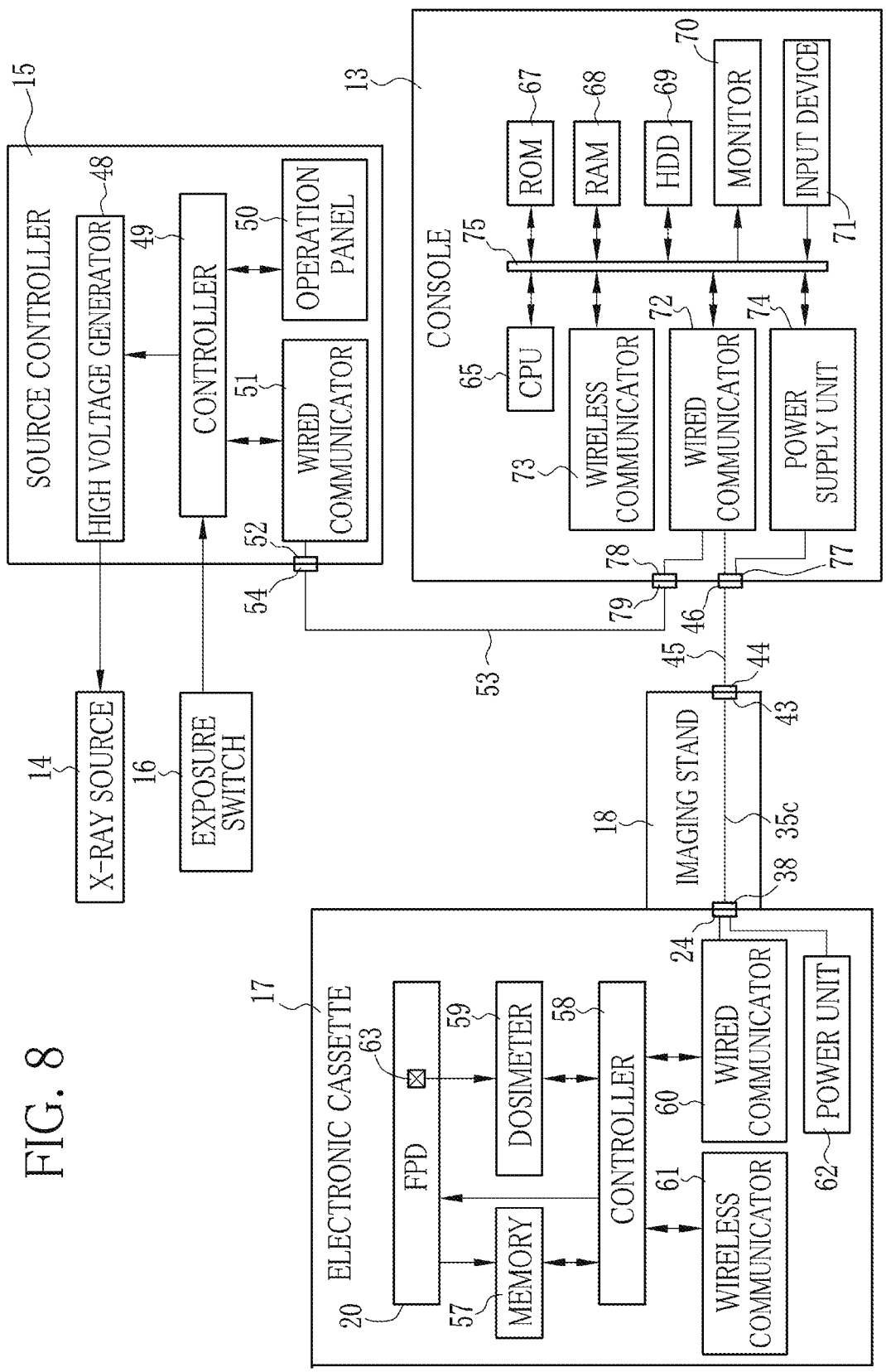
FIG. 8 is a block diagram of the X-ray image capturing system.

As shown in FIG. 8, the source controller 15 includes a high voltage generator 48, a controller 49, an operation panel 50, and a wired communicator 51. The high voltage generator 48 supplies high voltage to the X-ray source 14. The controller 49 controls a tube voltage for determining an energy spectrum of the X-rays from the X-ray source 14, a tube current for determining an X-ray irradiation amount per unit of time, and an X-ray irradiation duration. The operation panel 50 is used for operation of the X-ray generating apparatus 11. The wired communicator 51 is used for communication with the console 13. A communication terminal is connected to the wired communicator 51. To the communication terminal 52, a communication connector 54 of a communication cable 53 extending from the console 13 is connected.

The high voltage generator 48 produces the high tube voltage by multiplying an input voltage using a transformer, and supplies drive power to the X-ray source 14 through a high voltage cable. An exposure condition including the tube voltage, the tube current, and the X-ray irradiation duration is set up manually by a radiological technician from the operation panel 50. Note that, the exposure condition may be set up in the source controller 15 from the console 13 connected through the wired communicator 51.

The exposure switch 16, which is operated by the radiological technician, is connected to the source controller 15 through a communication cable. The exposure switch 16 is a two-step switch. Upon a first-step operation of the exposure switch 16, a warm-up start signal is issued to start warming up the X-ray source 14. Upon a second-step operation of the exposure switch 16, an irradiation start signal is issued to make the X-ray source 14 start emitting the X-rays. These signals are inputted to the source controller 15 through the communication cable.

The controller 49 controls the operation of the X-ray source 14 based on the signals from the exposure switch 16. Upon reception of the irradiation start signal from the exposure switch 16, the controller 49 issues a start command to the X-ray source 14, and starts supplying electric power to the X-ray source 14. At the same time, the controller 49 transmits a synchronization signal that notifies the console 13 of the start of X-ray emission through the wired communicator 51, and furthermore, actuates a timer to start measuring time from the start of X-ray emission.

When an emission stop signal from the console 13 is received or the measurement time reaches the X-ray irradiation duration set up in the exposure condition, the controller 49 issues an emission stop command to the source controller 15 to stop electric power supply to the X-ray source 14. The X-ray irradiation duration varies depending on the exposure condition. In taking a static image, the X-ray irradiation duration is set at the order of approximately 500 msec to 2 sec at the maximum.

The electronic cassette 17 is provided with the FPD 20 for producing the X-ray image, a memory 57 for storing the X-ray image, a controller 58 for controlling the entire electronic cassette 17, a dosimeter 59 for measuring an X-ray dose passed through the patient P, a wired communicator 60 and a wireless communicator 61 for establishing communication with the console 13, and a power unit 62 for supplying electric power to each part of the electronic cassette 17.

The wired communicator 60 uses a communication line such as a communication cable as a transmission line, and is connected to the multi terminal 24. In a case where the electronic cassette 17 is mounted on the imaging stand 18, the wired communicator 60 is connected to the console 13 through the multi terminal 24, the multi connector 38 of the imaging stand 18, the relay cable 35c, the external connection terminal 43, the multi connector 44, and the multi cable 45. The wireless communicator 61 uses an electromagnetic wave as a transmission line.

The wireless communicator 61 is used for establishing communication with the console 13 in the case of using the electronic cassette 17 without being mounted on the imaging stand 18. For example, in radiography of a patient P who is hard to stand up or radiography of a body part that is hard to take with the imaging stand 18, the electronic cassette 17 is used without being mounted on the imaging stand 18. In such radiography, the electronic cassette 17 is put under the patient P who lies on a bed or held by the patient P himself/herself. The wireless communicator 61 is usable in such occasions with ease, without the need for routing the multi cable 45.

The power unit 62 includes a rechargeable battery, a charging circuit for recharging the battery, and a power supply circuit for supplying electric power from the rechargeable battery to each part. The power unit 62 receives power supply from the console 13 through the multi terminal 24 connected thereto. In the case of using the electronic cassette 17 by itself, the electric power is supplied from the rechargeable battery to each part. In the case of supplying the electric power from the console 13 through the multi connector 38 connected to the multi terminal 24, the electric power from the console 13 is distributed to each part.

The FPD 20 is of an indirect conversion type, for example, having a matrix substrate and a scintillator (phosphor). In the matrix substrate, a plurality of pixels each of which is composed of a thin film transistor (TFT) and a photodiode are arranged in two dimensions. The scintillator converts the X-rays into visible light. The pixels perform photoelectric conversion of the visible light produced by the scintillator. The scintillator is opposed to an entire area of the arrangement of the pixels. Note that, a direct conversion type FPD, which has a conversion layer (amorphous selenium or the like) for directly converting the X-rays into electric charge, may be used instead.

The FPD 20 performs an accumulation operation, a readout operation, and a reset operation. In the accumulation operation, while the TFT is turned off, the photodiode accumulates signal charge by an amount corresponding to the amount of the X-rays incident thereon. In the readout operation, upon turning on the TFT, the signal charge is read out from the photodiode. In the reset operation, electric charge accumulated by dark current in the photodiode is discharged. The signal charge readout of each pixel in the readout operation is converted into a voltage signal by an integration amplifier. The voltage signal is converted into a digital signal by an A/D converter, so digital image data is outputted from the FPD 20 and is stored in the memory 57.

The FPD 20 includes one or more X-ray detection sensors 63 for use in automatic exposure control (AEC) of the dosimeter 59 in its irradiation surface 22. As the X-ray detection sensor 63, for example, is used a short pixel in which the TFT is short to constantly output the signal charge produced upon the incident X-rays.

The dosimeter 59 integrates the voltage signal read out of the X-ray detection sensor 63 to calculate a total X-ray dose, and inputs a calculation result to the controller 58. The controller 58 compares the calculation result of the dosimeter 59 with a threshold value, which is a value of the X-rays necessary for the radiography. If the total X-ray dose reaches the threshold value, the emission stop signal is transmitted to the source controller 15 through the wired communicator 60. The controller 58 ends the accumulation operation of the FPD 20 concurrently with the transmission of the emission stop signal, and puts the FPD 20 into the readout operation.

The console 13 is provided with a CPU 65 for controlling the operation of the entire system 10, a ROM 67 for storing in advance various types of programs including a control program, a RAM 68 for temporarily storing various types of data, and a HDD 69 for storing various types of data, a monitor 70 for displaying an exposure order, the X-ray image and the like, an input device 71 for entering the exposure condition, a wired communicator 72 and a wireless communicator 73 for establishing communication with the source controller 15 and the electronic cassette 17, and a power supply unit 74 for supplying electric power to the electronic cassette 17. All the above components are connected via a data bus 75.

To the wired communicator 72, a multi terminal 77 and a communication terminal 78 for use in communication and power supply are connected. The multi connector 46 of the multi cable 45 extending from the electronic cassette 17 through the imaging stand 18 is connected to the multi terminal 77. A communication connector of the communication cable 53 extending from the source controller 15 is connected to the communication terminal 78.

The console 13 receives entry of an examination order, which includes information about sex and age of the patient and an examination purpose, and displays the examination order on the monitor 70. The examination order is inputted from an external system e.g. HIS (hospital information system) or RIS (radiography information system) that manages patient data and examination data related to radiography, or inputted manually by the radiological technician from the input device 71. The radiological technician checks the contents of the examination order on the monitor 70, and inputs the exposure condition from the input device 71 in accordance with the contents of the examination order.

The console 13 transmits the exposure condition to the electronic cassette 17 to set up a signal processing condition of the FPD 20. Also, the console 13 mediates the transmission and reception of the synchronization signal for indicating the start of X-ray emission and the emission stop signal for commanding the stop of X-ray emission. Thereby, the console 13 performs synchronization control to synchronize the start/end timing of X-ray emission by the X-ray generating apparatus 11 and the accumulation/read out operation of the FPD 20.

The console 13 applies various types of image processing such as gamma correction, frequency processing, and the like to the image data outputted from the electronic cassette 17. The X-ray image after being subjected to the image processing is displayed on the monitor 70 of the console 13. The X-ray image is also stored to a data storage device, e.g. the HDD 69 of the console 13 or an image server connected to the console 13 through a network.

The power supply unit 74 is connected to the multi terminal 77, and supplies electric power to the electronic cassette 17 through the imaging stand 18. The wireless communicator 73 establishes communication with the electronic cassette 17, when the electronic cassette 17 is used without being mounted on the imaging stand 18.

The operation of the above embodiment will be described. In radiography using the X-ray image capturing system 10, as shown in FIG. 4, the tray 30 is drawn out of the cassette holder 28 of the imaging stand 18 with the use of the grip 34. The electronic cassette 17 is mounted on the tray 30 using the first and second catch members 35 and 36 in such a position that the irradiation surface 22 of the electronic cassette 17 is directed forward (a rear surface of the electronic cassette 17 is opposed to the mount board 30*a*).

Figure 6B:
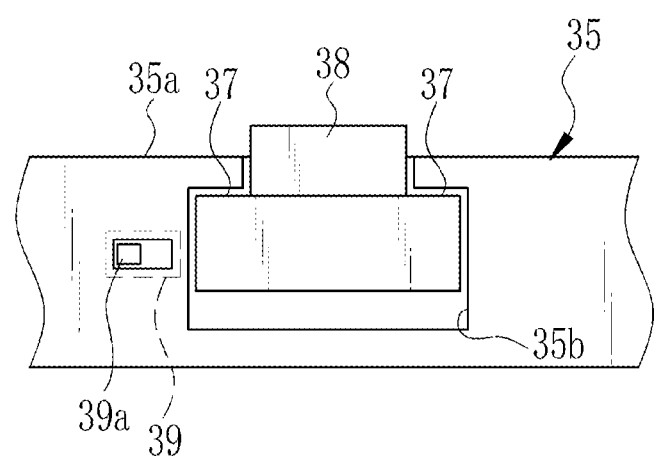
FIG. 6B is an explanatory view of the multi connector in a projected position.

To be more specific, as shown in FIG. 6B, the multi connector 38 of the first catch member 35 is moved to the projected position, and the lock mechanism 39 locks the multi connector 38. After that, the electronic cassette 17 is positioned properly relative to the first catch member 35 such that the multi connector 38 faces to the multi terminal 24. In this state, the second catch member 36 is moved such that the electronic cassette 17 is caught between the first and second catch members 35 and 36. Then, the first side surface 21*a* of the electronic cassette 17 is made contact with the catch surface 35*a* of the first catch member 35. Since the multi connector 38 and the multi terminal 24 are opposed to each other, the multi connector 38 is fitted into and connected to the multi terminal 24 by the contact between the first side surface 21*a* and the catch surface 35*a*. The bias of the spring provided in the second catch member 36 makes the second catch member 36 contact the second side surface 21*b* of the electronic cassette 17. Thereby, the first and second catch members 35 and 36 catch the electronic cassette 17. The electronic cassette 17 is mounted on the tray 30 in this manner.

After the mounting of the electronic cassette 17 on the tray 30, the multi connector 44 of the multi cable 45 is connected to the external connection terminal 43. After that, the tray 30 is loaded into the cassette holder 28. In a loaded state, the irradiation surface 22 of the electronic cassette 17 faces to the imaging surface 31 of the imaging stand 18. The multi terminal 24 of the electronic cassette 17 is offset with respect to the center line C1 of the irradiation surface 22. In a state where the tray 30 is loaded into the cassette holder 28, the multi connector 38 is offset with respect to the center line C2 of the imaging surface 31 in the same direction by the same amount as those of the multi terminal 24. Accordingly, when the tray 30 is loaded into the cassette holder 28, the center line C1 of the irradiation surface 22 of the electronic cassette 17 mounted on the tray 30 aligns with the center line C2 of the imaging surface 31. The connection between the multi cable 45 and the external connection terminal 43 is performed after the mounting of the electronic cassette 17 on the tray 30, but may be performed before the mounting.

The electronic cassette 17 is connected to the console 13 through the multi terminal 24, the multi connector 38, the relay cable 35*c*, the external connection terminal 43, and the multi cable 45. The electronic cassette 17 is electrically connected to the console 13, so the communication between the electronic cassette 17 and the console 13 is established, and the electric power is supplied from the console 13 to the electronic cassette 17.

The height of the cassette holder 28 of the imaging stand 18 is adjusted in accordance with the height of the patient's body part to be examined. The height of the X-ray source 14 and the size of the X-ray irradiation field are adjusted in accordance with the height of the cassette holder 28 and the size of the electronic cassette 17. Then, the electronic cassette 17 is turned on. In the console 13, the exposure condition is inputted from the input device 71, and is set up by the CPU 65. The CPU 65 transmits the exposure condition to the wired communicator 60 of the electronic cassette 17 through the wired communicator 72. The controller 58 of the electronic cassette 17 determines the threshold value of the total X-ray dose based on the received exposure condition. To the source controller 15, the exposure condition including the tube voltage, the tube current, and the X-ray irradiation duration is set up from the operation panel 50.

The console 13 transmits an exposure preparation command for commanding preparation for radiography to the electronic cassette 17 through the wired communicator 72. Upon reception of the exposure preparation command, the FPD 20 of the electronic cassette 17 is put into a ready mode. Upon input of the irradiation start signal from the exposure switch 16, the source controller 15 issues the emission start command to the X-ray source 14. The X-ray source 14 starts X-ray emission to the patient P. Concurrently, the source controller 15 transmits the synchronization signal to the electronic cassette 17 through the console 13. Upon receiving the synchronization signal, the controller 58 of the electronic cassette 17 puts the FPD 20 into the accumulation operation.

The dosimeter 59 measures the total X-ray dose passed through the patient P by integration of the output voltage of the X-ray detection sensor 63 during the accumulation operation of the FPD 20, and inputs a measurement result to the controller 58. The controller 58 compares the total X-ray dose with the threshold value. If the total X-ray dose reaches the threshold value, the controller 58 makes the wired communicator 60 transmit the emission stop signal to the source controller 15 through the console 13. In response to the emission stop signal, the source controller 15 issues the emission stop command to the X-ray source 14 to stop X-ray emission. Concurrently with the transmission of the emission stop signal, the controller 58 shifts the FPD 20 from the accumulation operation to the readout operation. The readout X-ray image data is transmitted from the electronic cassette 17 to the console 13, and is stored to the HDD 69 after being subjected to the predetermined image processing. Since the electronic cassette 17 and the console 13 establish wired communication, which is superior to the wireless communication in communication delay, the AEC is carried out with precision.

As described above, according to the present invention, it is unnecessary to connect a multi cable to the electronic cassette 17 in mounting the electronic cassette 17 on the imaging stand 18. Thus, the multi cable does not hinder the mounting or does not cause troublesome task such as routing. Since the multi cable 45 is securely connected to the imaging stand 18, the multi connector 44 is hardly unmated on the occasion of mounting the electronic cassette 17 on the imaging stand 18 or the occasion of moving the cassette holder 28 with the electronic cassette 17.

The multi terminal 24 of the electronic cassette 17 and the multi connector 38 of the first catch member 35 are securely connected with taking advantage of force that is caused by the first and second catch members 35 and 36 catching the electronic cassette 17 therebetween.

Since the positional relation between the center line C2 of the imaging surface 31 and the multi connector 38 is the same as that between the center line C1 of the irradiation surface 22 and the multi terminal 24, the center line C2 of the imaging surface 31 is easily aligned with the center line C1 of the irradiation surface 22 only by the connection between the multi connector 38 and the multi terminal 24. Thus, the positioning between the electronic cassette 17 and the imaging stand 18 is easily carried out.

As in the case of the electronic cassettes 40 and 41 (see FIG. 7A), even if the housing and the irradiation surface have a variety of sizes, the electronic cassette 40 or 41 is mounted on the imaging stand 18 so as to align the center line C1 of the irradiation surface 22 with the center line C2 of the imaging surface 31. Since the positions of the multi terminal 24 and the multi connector 38 are determined with respect to the center line C1 of the irradiation surface 22 and the center line C2 of the imaging surface 31, respectively, it is possible to carry out the positioning between the electronic cassette 17 and the imaging stand 18 irrespective of the variety of sizes of the housing and the irradiation surface. Therefore, the positioning between the electronic cassette 17 and the imaging stand 18 is easily carried out even if the electronic cassette of any size is mounted on the imaging stand 18.

Figure 9:
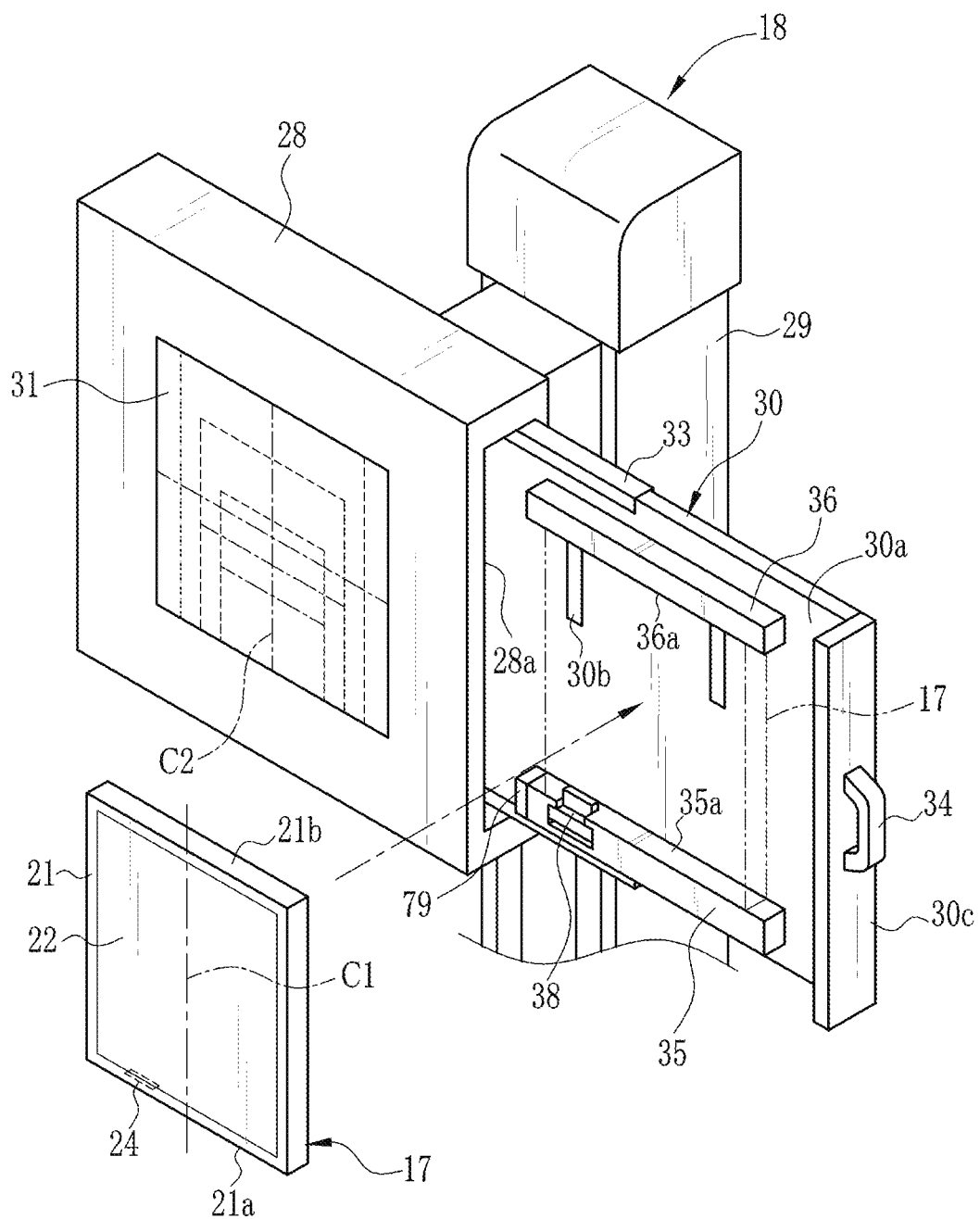
FIG. 9 is a perspective view of an imaging stand according to a second embodiment in a state of pulling out a tray.

Next, a second embodiment of the present invention will be described. The same components as above are referred to the same reference numerals as those of the first embodiment, and description thereof will be omitted. In this embodiment, as shown in FIGS. 9 and 10, the column 29 of the imaging stand 18 is provided at its side surface with an external connection terminal 82 to which a multi cable 83 extending from the console 13 is connected. The external connection terminal 82 is connected to the multi connector 38 through a first relay terminal 79, a second relay terminal 80, and a relay cable 81.

The first relay terminal 79 is provided in the first catch member 35, as with the external connection terminal 43 (see FIGS. 4 and 5) of the first embodiment. However, in contrast to the external connection terminal 43, the first relay terminal 79 is provided on a surface of the first catch member 35 opposite to the surface of the external connection terminal 43, in other words, the side surface on the opposite side of the tray insertion slot 28a in a state where the tray 30 is loaded into the cassette holder 28. The second relay terminal 80 is disposed inside the cassette holder 28. The second relay terminal 80 to be directly connected to the first relay terminal 79 is positioned in the depths of the tray insertion slot 28a so as to face the first relay terminal 79. The second relay terminal 80 is connected to the first relay terminal 79 when the tray 30 is loaded into the cassette holder 28. The second relay terminal 80 is disconnected from the first relay terminal 79 when the tray 30 is unloaded from the cassette holder 28.

The relay cable 81 routed through the column 29 and the cassette holder 28 mediates between the external connection terminal 82 and the second relay terminal 80. To the external connection terminal 82, a multi connector 84 of a multi cable 83 is connected. In the second embodiment, the electronic cassette 17 is connected to the multi cable 83 extending from the console 13 through the multi connector 38, the first relay terminal 79, the second relay terminal 80, the relay cable 81, and the external connection terminal 82. Note that, the above structure of the relay terminal and the relay cable for relaying between the external connection terminal 82 and the multi connector 38 is just an example, and the number of the relay terminals and the relay cables is appropriately changeable.

The second embodiment, in contrast to the first embodiment, can eliminate the need for mating the multi cable 45 to the external connection terminal 43 inside the tray 30, so preparation for radiography becomes easier. The second embodiment eliminates the need for drawing the multi cable 45 out of the cassette holder 28, and hence the multi cable does not hinder the vertical movement of the cassette holder 28 along the column 29.

In the above embodiments, the multi terminal 24 and the multi connector 38 are offset to the left with respect to the center line C1 of the irradiation surface 22 and the center line C2 of the imaging surface 31, respectively, but may be offset to the right instead. The length L being an offset amount with respect to the center lines C1 and C2 can take an arbitrary value, and for example, is determined in consideration of the minimum size of a plurality of types of electronic cassettes to be mounted on the imaging stand. This is because if the offset amount is determined based on the electronic cassette of maximum size, the offset amount cannot be always applicable to the electronic cassette of minimum size.

Figure 11A:
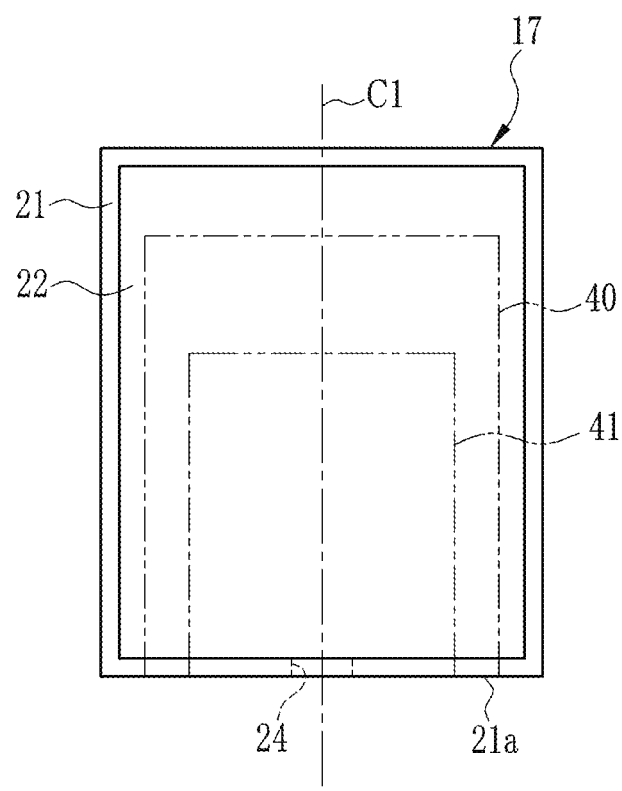
FIG. 11A is a top plan view of an electronic cassette that represents the position of a multi terminal in the case of setting an offset amount at "0"
Figure 11B:
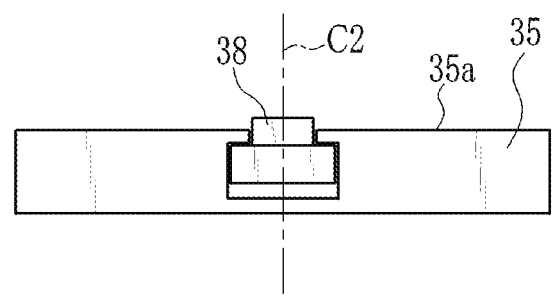
FIG. 11B is a sectional view of a first catch member and a multi connector that represents the position of the multi connector in the case of setting the offset amount at "0"

The offset amount (length L) may be half of the width of the multi terminal 24 and the multi connector 38 or less. Since the offset amount is determined with respect to the center of the multi terminal 24 and the multi connector 38 in the above embodiments, if the offset amount is half of the width of the multi terminal 24 and the multi connector 38 or less, the multi terminal 24 and the multi connector 38 are disposed above the center lines C1 and C2, respectively. As shown in FIGS. 11A and 11B, the offset amount may be further reduced to "0". If the offset amount is "0", the centers of the multi terminal 24 and the multi connector 38 in the width direction coincide with the center lines C1 and C2, respectively.

Figure 12A:
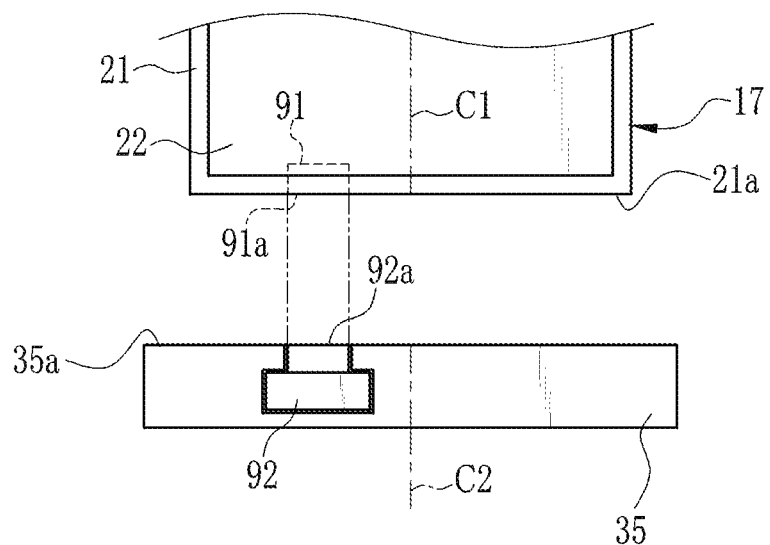
FIG. 12A is an explanatory view of a multi terminal and a multi connector that have a contact surface in an unmating state.
Figure 12B:
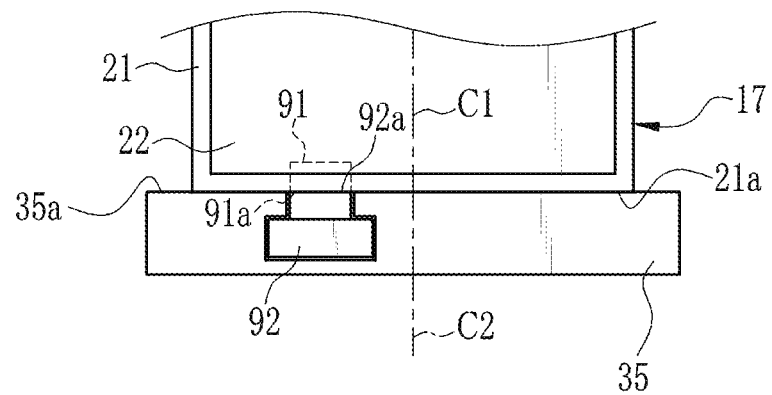
FIG. 12B is an explanatory view of the multi terminal and the multi connector of FIG. 12A in a mating state.

In the above embodiments, a female terminal is used as the multi terminal 24 of the electronic cassette 17, and a male connector fitted into the female terminal is used as the multi connector 38 of the imaging stand 18. Instead of the male or female fitting, a surface contact type of terminal and connector may be used as shown in FIGS. 12A and 12B. A surface contact type of multi terminal 91 and multi connector 92 have flat contact surfaces 91a and 92a, respectively, instead of a male or female fitting portion. The contact surface 91a of the multi terminal 91 is exposed to the outside in a state of approximately coplanar to the first side surface 21a of the housing 21. The contact surface 92a of the multi connector 92 is also exposed to the outside in a state of approximately coplanar to the catch surface 35a of the first catch member 35. The position of the multi connector 92 is fixed and immovable, while the multi connector 38 of the above embodiments is movable between the projected position projected from the catch surface 35a and the retracted position.

As shown in FIG. 12B, by pressing the catch surface 35a of the first catch member 35 against the first side surface 21a, the contact surface 91a of the multi terminal 91 comes into contact with the contact surface 92a of the multi connector 92, so the connection between the multi terminal 91 and the multi connector 92 is completed. The use of the multi terminal 91 and the multi connector 92 can eliminate the need for providing the multi connector 38 movable between the projected position and the retracted position in the catch surface 35a of the first catch member 35. Therefore, this embodiment facilitates the mounting of the film cassette and the IP cassette.

To reliably contact the contact surface 91a of the multi terminal 91 to the contact surface 92a of the multi connector 92, it is preferable that one or both of the contact surfaces 91a and 92a are slightly protruded from the catch surface 35a and the first side face 21a, respectively. This protrusion amount is sufficiently small so as not to hinder the mounting of the film cassette and the IP cassette. In the present invention, the state of the contact surfaces 91a and 92a being flat relative to the catch surface 35a and the first side surface 21a, respectively, includes a state where the catch surfaces 91a and 92a are slightly protruded within a range of not affecting the mounting of the film cassette and the IP cassette.

Figure 13:
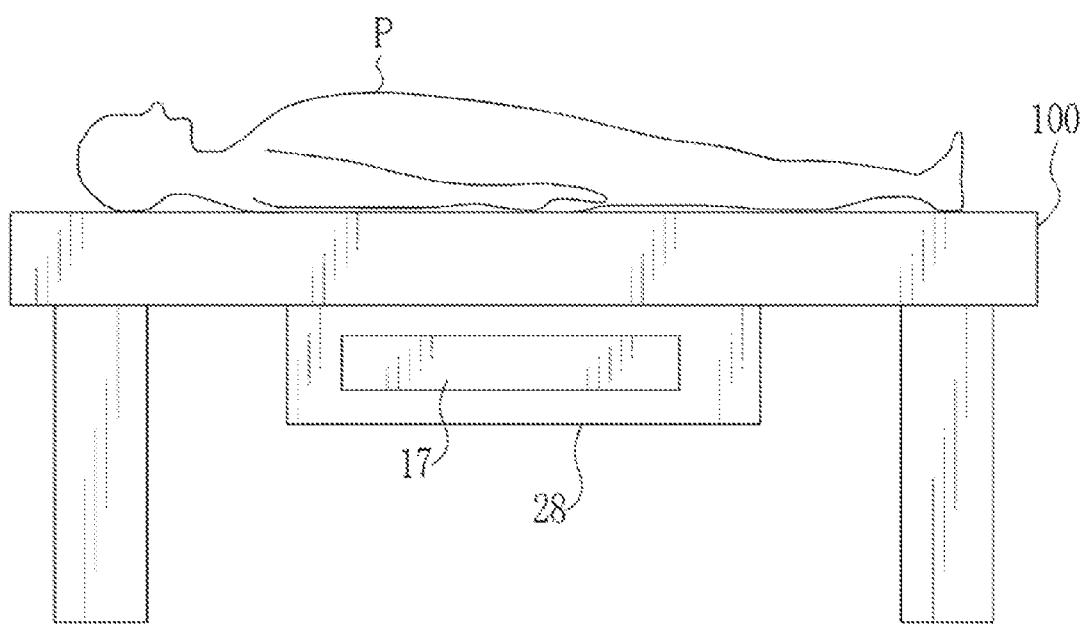
FIG. 13 is an explanatory view showing schematic structure of an alternative embodiment of an X-ray image capturing system, implemented as part of a bed.

In each of the above embodiments, the first and second catch members 35 and 36 catch the electronic cassette 17 from above and below, but may catch the electronic cassette 17 in its width direction. The first catch member 35 may be movable in addition to the second catch member 36. Instead of the imaging stand 18, the present invention is applicable to an imaging table 100 in which a bed having the electronic cassette is movable horizontally and vertically to perform radiography of the patient in a lying position, as shown in FIG. 13.

The AEC function may be stopped when the connector of the communication cable is unmated from the connection terminal of the electronic cassette. This control may be performed by monitoring the connection between the connector and the terminal using a sensor or the like. In another case, the electronic cassette or the console may transmit a signal for checking the connection therebetween, and the connection may be confirmed based on the presence or absence of a response signal.

The AEC function may be omitted. The wired communication between the electronic cassette and the console is absolutely necessary for use of the AEC function, as a matter of course. However, the wired communication is required in other occasions, for example, in the case of using the electronic cassette in environment where incoming signal strength is weak. The control signal is transmitted from the console to the electronic cassette, and the X-ray image data is transmitted from the electronic cassette to the console. Thus, even without the use of the AEC function, if the incoming signal strength is too weak to establish the wireless communication, the electronic cassette and the console are connected through the cable.

Even in the wired communication without using the AEC function, if the electronic cassette is used in a state of being mounted on the imaging stand, it is possible to obtain the effects of the present invention, that is, to facilitate the positioning between the electronic cassette and the imaging stand and to easily establish wired communication between the electronic cassette and the external device such as the console.

The electronic cassette has the multi terminal that provides both the communication and the power supply, and the imaging stand has the multi connector that provides both the communication and the power supply. However, the terminal and the connector are not necessarily of a multi type. For example, there is a case where the electric power is supplied through a cable to recharge the battery, while the other signals are transmitted through the wireless communication. On the other hand, there is a case where the wired communication is established due to the weak incoming signal strength, while the battery power is enough. The above effects of the present invention are obtained even in such cases.

The short pixel is used for measuring the total X-ray dose, but the X-ray dose may be measured in another way. For example, bias voltage is applied to the photodiode composing the pixel, and bias current flowing through a bias line varies in accordance with the amount of the signal charge produced in the photodiode. The bias current may be detected to measure the X-ray dose. As further another way, in a state where the TFT of the pixel is turned off, slight leak current flows through the signal line in accordance with the amount of the signal charge produced in the photodiode. The leak current may be detected to measure the X-ray dose.

The FPD of a TFT type in which the TFT matrix substrate is formed in the glass substrate is used in the above embodiments, but another type of FPD using a CMOS image sensor or a CCD image sensor formed in a semiconductor substrate may be used instead. The use of the CMOS image sensor has the following merit. The CMOS image sensor can perform the so-called nondestructive readout, by which the signal charge accumulated in each pixel is readout as a voltage signal through an amplifier provided in each pixel without being discharged into the signal line. Accordingly, even during the accumulation operation, it is possible to choose an arbitrary pixel from an imaging area, and read out the signal charge from the pixel to measure the X-ray dose. Therefore, in the CMOS image sensor, any normal pixel is usable as a detection element for measuring the X-ray dose, instead of preparing a detection element specific to the measurement.

The controller 58 controls the entire electronic cassette 17 in the above embodiments, but the present invention is also applicable to an X-ray imaging apparatus that has an electronic cassette having an FPD and an external control device connected to the electronic cassette through wired or wireless communication. In this case, the external control device is connected through a cable to the imaging stand 18 on which the electronic cassette 17 is mounted.

The present invention is applicable to a radiation imaging apparatus using another type of radiation such as γ-rays, instead of the X-rays.

Although the present invention has been fully described by the way of the preferred embodiment thereof with reference to the accompanying drawings, various changes and modifications will be apparent to those having skill in this field. Therefore, unless otherwise these changes and modifications depart from the scope of the present invention, they should be construed as included therein.

What is claimed is:

1. A radiation imaging apparatus comprising:
    an electronic cassette and an imaging stand or an imaging table for detachably mounting said electronic cassette thereon, said electronic cassette having a flat panel detector for detecting a radiographic image and a housing containing said flat panel detector, said radiation imaging apparatus further comprising:
    an irradiation surface formed in a surface of said housing, for receiving irradiation with radiation;
    a connection terminal provided in a first side surface of said housing, said first side surface being orthogonal to said irradiation surface;
    an imaging surface provided in said imaging stand or imaging table, said imaging surface facing said irradiation surface in a state where said electronic cassette is mounted on said imaging stand or imaging table;
    first and second catch members provided in said imaging stand or imaging table, said first catch member coming in contact with said first side surface of said housing and said second catch member coming in contact with a second side surface opposed to said first side surface so as to catch said electronic cassette and hold said electronic cassette in a state of facing said irradiation surface to said imaging surface;
    a connector provided in said first catch member, said connector being connected to said connection terminal when said electronic cassette is held on said imaging stand or imaging table;
    a cassette holder provided in said imaging stand or imaging table, said cassette holder having said imaging surface; and
    a tray provided in said imaging stand or imaging table, said tray having said first and second catch members and being insertable into and pullable out of said cassette holder, and a catch of said electronic cassette with said first and second catch members allowing connection between said connection terminal and said connector and mounting of said electronic cassette on said tray, wherein
    said tray is pulled out of said cassette holder in a direction orthogonal to a catching direction of said electronic cassette with said first and second catch members.

2. The radiation imaging apparatus according to claim 1, wherein
    said imaging stand or imaging table has an external connection terminal, to which a cable extending from an external device disposed outside said imaging stand or imaging table is connected, so as to electrically connect said electronic cassette to said external device through said connection terminal and said connector;
    said connection terminal is offset with respect to a center line of said irradiation surface;
    said connector is offset with respect to a center line of said imaging surface by a same amount in a same direction as those of said connection terminal; and
    said external connection terminal is provided such that said cable is drawn out to a side opposite to said connector with respect to the center line of said irradiation surface in a direction orthogonal to said catching direction.

3. The radiation imaging apparatus according to claim 2, wherein said external connection terminal is provided in said first catch member.

4. The radiation imaging apparatus according to claim 1, wherein said first and second catch members extend in a direction orthogonal to a center line of said imaging surface.

5. The radiation imaging apparatus according to claim 2, wherein said imaging stand or imaging table has at least one relay terminal for relaying between said external connection terminal and said connector.

6. The radiation imaging apparatus according to claim 5, wherein
    said relay terminal includes a first relay terminal provided in said first catch member and a second relay terminal provided in said cassette holder;
    said first and second relay terminals are connected by loading said tray into said cassette holder; and
    said first and second relay terminals are disconnected by unloading said tray from said cassette holder.

7. The radiation imaging apparatus according to claim 1, wherein said electronic cassette includes an automatic exposure controller, and said automatic exposure controller includes:
    a dosimeter for measuring a dose of said radiation emitted from a radiation source and passed through a human body;
    a controller for comparing a measurement result of said dosimeter with a threshold value; and
    a communicator established by connection between said connection terminal and said connector, wherein
    when said measurement result reaches said threshold value, said controller sends an emission stop signal through said communicator to said radiation source to stop emission of said radiation.

8. The radiation imaging apparatus according to claim 1, wherein said connection terminal and said connector connect said electronic cassette to an external device for controlling said electronic cassette in order to establish communication between said electronic cassette and said external device.

9. The radiation imaging apparatus according to claim 1, wherein said connection terminal and said connector connect said electronic cassette to an external device in order to supply electric power from said external device to said electronic cassette.

10. The radiation imaging apparatus according to claim 1, wherein
    said connection terminal is a multi terminal that is integrally formed with a communication terminal for communicating with an external device and a power terminal for supplying electric power to said electronic cassette; and
    said connector is a multi connector that is integrally formed with a communication connector for communicating with said external device and a power connector for supplying the electric power to said electronic cassette.

11. The radiation imaging apparatus according to claim 1, wherein said first and second catch members catch said electronic cassette from above and below.

* * * * *